United States Patent [19]
Ahlem et al.

[11] Patent Number: 5,650,512
[45] Date of Patent: Jul. 22, 1997

[54] FLUORESCENT LABELING REAGENTS

[75] Inventors: Clarence N. Ahlem, Bellevue, Wash.; Steven M. Torkelson, San Mateo, Calif.

[73] Assignee: Systemix, Palo Alto, Calif.

[21] Appl. No.: 484,961

[22] Filed: Jun. 7, 1995

[51] Int. Cl.$^6$ .............................................. C07D 491/22
[52] U.S. Cl. .................................................. 546/37
[58] Field of Search ........................... 546/37; 436/91, 436/96, 97, 172

[56] References Cited

U.S. PATENT DOCUMENTS

| | | | |
|---|---|---|---|
| 4,609,689 | 9/1986 | Schwartz et al. | 523/202 |
| 4,713,348 | 12/1987 | Ullman | 435/7.25 |
| 4,745,181 | 5/1988 | Law et al. | 530/391.5 |
| 5,441,935 | 8/1995 | Rozengurt et al. | 514/15 |
| 5,453,517 | 9/1995 | Kuhn et al. | 549/227 |

OTHER PUBLICATIONS

Titus, J.A. et al J. Immunol. Meth. 1982, 50, page 193–204.

Edwards, R.J. et al J. Immunol. Meth. 1989, 117, pp. 215–220.

Abuelyaman, A.S. et al Bioconjugate Chem. 1994, 5, pp. 400–405.

*Primary Examiner*—C. Warren Ivy
*Assistant Examiner*—Garth M. Dahlen
*Attorney, Agent, or Firm*—Blakely, Sokoloff, Taylor & Zafman

[57] ABSTRACT

A class of sulforhodamine labeling reagents capable of binding with a biomolecular species to produce a conjugate with fluorescent properties. The sulforhodamine labeling reagents have the structure:

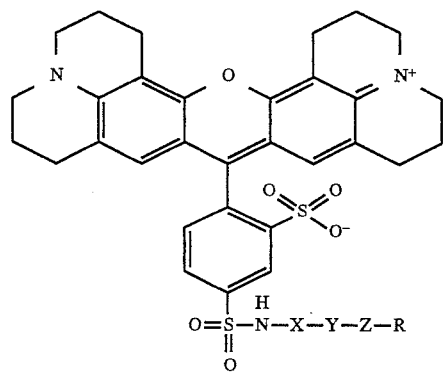

The group X is selected from an alkyl, an olefin, a monocyclic aliphatic saturated hydrocarbon, an aryl, or nothing at all. The group Y is selected from an amide, a substituted amide, or nothing at all. The group Z is selected from a monocyclic aliphatic hydrocarbon, an aryl, or an alkyl, as defined with respect to group X, a polyethylene glycol chain of the general form $(CH_2CH_2O)_n$, or nothing at all. The alkyl or polyethylene glycol chain may further have inert intermediate amide, ether, or disulfide functionalities. The group X, group Y, and group Z cannot all be nothing at all or non-existent. The group R is an electrophilic moiety suitable for conjugation of the fluorescent labeling reagent with a biomolecular species. Also disclosed is a method of making the reagents.

2 Claims, 7 Drawing Sheets

(1) POCl₃
(2) H₂N―∕∖―NH₂

FLUORESCENT LABELING REAGENTS

FIELD OF THE INVENTION

The present invention relates to the field of fluorophores and to the field of conjugation of biomolecules with reactive probes for labeling and study of cytometry, and more particularly to a class of sulforhodamine labeling reagents and methods of making such reagents.

BACKGROUND OF THE INVENTION

The chemical modification of proteins, nucleotides, and other biomolecules is an important research tool in immunology, histochemistry, biochemistry, and cell biology. Conjugation is a form of modification in which two or more molecules with distinct properties are joined so that some of the characteristics of each joined molecule are retained in the product. For example, molecules with special properties of fluorescence or binding specificity can be covalently bound or conjugated to a protein, DNA strand, or other biomolecule. Proteins, peptides, polysaccharides, hormones, nucleic acids and their analogs, and liposomes may be conjugated with each other or with molecular groups that add useful properties (e.g., drugs, radionuclides, toxins, fluorphores, photoprobes, inhibitors, enzymes, haptens, ligands).

Fluorescent dyes are routinely conjugated to biological molecules to impart the properties of light absorption and fluorescence to the biomolecule for a variety of purposes including separation and fluorescence imaging. For example, fluorescent labeling of antibody molecules is used extensively for applications such as immunohistological staining and cell separation by flow cytometry.

The chemical modification of biomolecules with fluorescent probes generally involve covalent attachment of the probe to the biomolecule, although many fluorophore probes for nucleic acids do not covalently bond to the target biomolecule. The most commonly exploited conjugation points for covalent bonding in proteins are the aliphatic amine groups, notably, the ϵ-amine groups of lysine and the α-amino groups of the N-terminal amino acids. Other conjugation points in proteins include thiol residues in cysteine and cystine, the phenolic hydroxyl group of tyrosine and carboxlic acid groups of aspartic acid and glutamic acid.

Fluorescent probes are chosen based upon their physical properties. The probe must be able to bind to a particular site on a biomolecule (i.e., amine or thiol group of a protein) and must be relatively specific for that particular binding site. A probe that is too reactive in the conjugation reaction solution (e.g. an aqueous solution) will hydrolyze before binding to the target site. In most cases, the fluorescent probe should also be relatively soluble in water so as not to precipitate out of solution and also be capable of reacting rapidly and specifically with a particular binding site at substantially neutral pH (and particularly physiological pHs).

The reaction kinetics of a fluorescent probe should be controllable. In other words, the amount of fluorescent label conjugated per biomolecule should be capable of being regulated. Regulation of the reaction kinetics is important to permit consistent reproducibility of labeling results. Regulation is also important because excess labeling can alter the biological characteristics of the biomolecule, e.g., it may lower the biomolecule's affinity for its target. In the case of labeling antibodies, for example, excessive substitution of the fluorescent probe to the antibody can reduce the affinity of the antibody for a particular antigen.

The fluorescent probe should have a relatively large extinction coefficient, that characterizes its light-absorbing power, at least in certain uses (e.g. fluorescent flow cytometry). The quantum yield should be large when the probe is bound to the target and is in the solvent environment where the fluorescence measurement is to be made. The fluorescent probe should also excite at desired wavelength levels, preferably above 500 nanometers to avoid autofluorescence from cell constituents. The photostability, or the number of excitations that a fluorescent probe can withstand is also important, especially for detecting a small number of probes in solution.

Common fluorescent labels include fluoroscein and rhodamines. Fluorescein has a relatively high extinction coefficient and quantum yield, and is generally soluble in aqueous solutions and easily conjugated to proteins. However, fluorescein is relatively photounstable and loses fluorescence below pH 8. Unfortunately, it is preferred to use a pH below 8 when a probe is conjugated to a protein in a living cell, and consequently fluoroscein's use in this context has some disadvantages. Fluorescein also has a wavelength of excitation in a region that produces autofluorescence.

Rhodamines excite in the 500 to 600 nanometer range, where less autofluorescence is generated. Rhodamines are more photostable than fluorescein and are pH insensitive under physiological conditions (pH 7–8). However, rhodamines have a relatively low quantum yield and limited solubility.

One of the most widely used rhodamines for amine-reactive fluorescent labeling is a sulfonyl halide derivative of rhodamine, sulforhodamine 101 acid chloride, or Texas Red (a trademark of Molecular Probes, Inc.). Sulforhodamine 101 compounds like Texas Red are particularly useful as fluorescent dyes since their spectra minimally overlap the spectra of fluorescein and other green dyes. Typically, sulforhodamine101 compounds exhibit fluorscence in the wavelength range of 610–630 nanometer. In comparison, fluorescein has a wavelength of exitation in the range of 500–520 nanometers. Therefore, fluorescein and sulforhodamine 101 are well-suited for two-color imaging and cell sorting.

Texas Red forms stable sulfonamide bonds that make it a popular amine-modifying reagent and thus it has proven to be very useful to label lysine groups on proteins and polypeptides generally. However, sulfonyl halides, like Texas Red, are highly reactive, are less specific, and hydrolyze easily prior to conjugation to the target site. Texas Red not only selectively reacts with amines, but also, through a competing reaction, tends to react with the solvent medium.

Further, the labeling of proteins with Texas Red is not kinetically controllable. The labeling results cannot be consistently reproduced and it is impossible to maintain the substitution ratio of Texas Red to biomolecule in any desired range depending on input ratios. Instead, the substitution ratio of Texas Red on a protein depends on intangibles like stir rate, order of mixing, and the size of the reaction particles.

Thus, there is a need for a rhodamine fluorescent probe that is kinetically controllable, is site specific but only moderately reactive, and will not hydrolyze too rapidly.

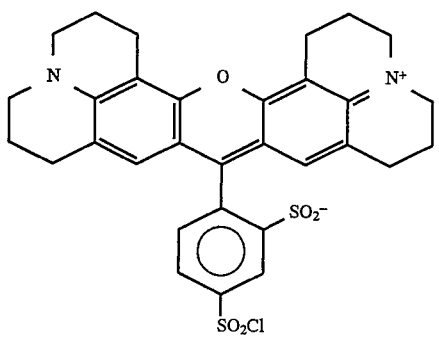

Texas Red

SUMMARY AND OBJECTS OF THE INVENTION

The invention relates to a novel class of fluorescent labeling reagents for conjugation to biomolecules. More specifically, the invention relates to a class of sulforhodamine labeling reagents that are desirable entities for biomolecular conjugation because the reagents can react rapidly, controllably, and specifically with target sites at near neutral pH without organic solvents. Unlike all other sulforhodamine labeling reagents that are extremely reactive and susceptible to hydrolysis, the reagents of the instant invention possess sufficient stability in aqueous solution to allow kinetic control of the conjugation reaction. Thus, optimal substitution ratios can be achieved and the results can be reproduced. Finally, the invention relates to the preparation of the labeling reagents described herein.

Labeling reagents suitable for the conjugation of a biomolecular species for the purpose of incorporating fluorescent properties have the general formula:

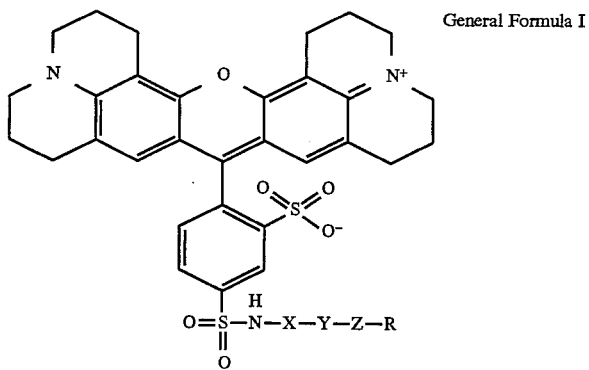

General Formula I

The group X is selected from an alkyl, an olefin, a monocyclic aliphatic saturated hydrocarbon, an aryl, or nothing at all. Alkyl denotes an acyclic saturated aliphatic straight or branched chain hydrocarbon. —$CH_2$, —$CH_2CH_2$, —$CH_2CH_2CH_2CH_2$— are examples of alkyls. A reasonably long alkyl chain (e.g., an alkyl chain of 5–10 carbon equivalents in length) may be used at group X because the overall reagent molecule is a zwiterion. An olefin denotes an unsaturated aliphatic hydrocarbon having the general formula $C_nH_{2n}$. —$CH_2CH=CHCH_2$— is an example of an olefin. An example of a monocyclic aliphatic saturated hydrocarbon is cyclohexane. An aryl is used to denote an aromatic ring, a substituted aromatic ring, and fused aromatic rings. Phenyl, hydroxyphenyl, and napthalene are examples of aryls.

The group Y is selected from an amide, a substituted amide, or an amide functional moiety, or nothing at all. An example of an amide is NHCO. An example of a substituted amide is $N(CH_3)CO$. The amide or substituted amide may be synthesized from an amide functional moiety such as an imidazole.

The group Z is selected from a monocyclic aliphatic hydrocarbon, an aryl, an alkyl or a polyethylene glycol chain of the general form $(CH_2CH_2O)_n$, or nothing at all. The alkyl or polyethylene glycol chain may further have inert intermediate functionalities, e.g., amide, ether, or disulfide functionalities. Again, a reasonably long alkyl or polyethylene glycol chain may be used at group X because the overall reagent molecule is a zwiterion.

Groups X, Y, and Z can all be nothing or non-existent. However, groups X, Y, and Z cannot be nothing or non-existent at the same time. For example, an embodiment is contemplated where group X and group Y are nothing or do not exist, but group Z does exist in the form of a monocyclic aliphatic hydrocarbon, an aryl, an alkyl or a polyethylene glycol chain of the general form $(CH_2CH_2O)_n$.

The group R is an electrophilic moiety suitable for conjugation of the fluorescent labeling reagent with a biomolecular species. Included as acceptable R groups are reactive esters, reactive amides, reactive disulfides, and maleimide functionalities.

Other objects, features, and advantages of the present invention will be apparent from the accompanying drawings and from the the detailed description that follows below.

BRIEF DESCRIPTION OF THE DRAWINGS

The present invention is illustrated by way of example and not limitation in the figures of the accompanying drawings, in which like references indicate similar elements and in which.

DETAILED DESCRIPTION

Figure 1:
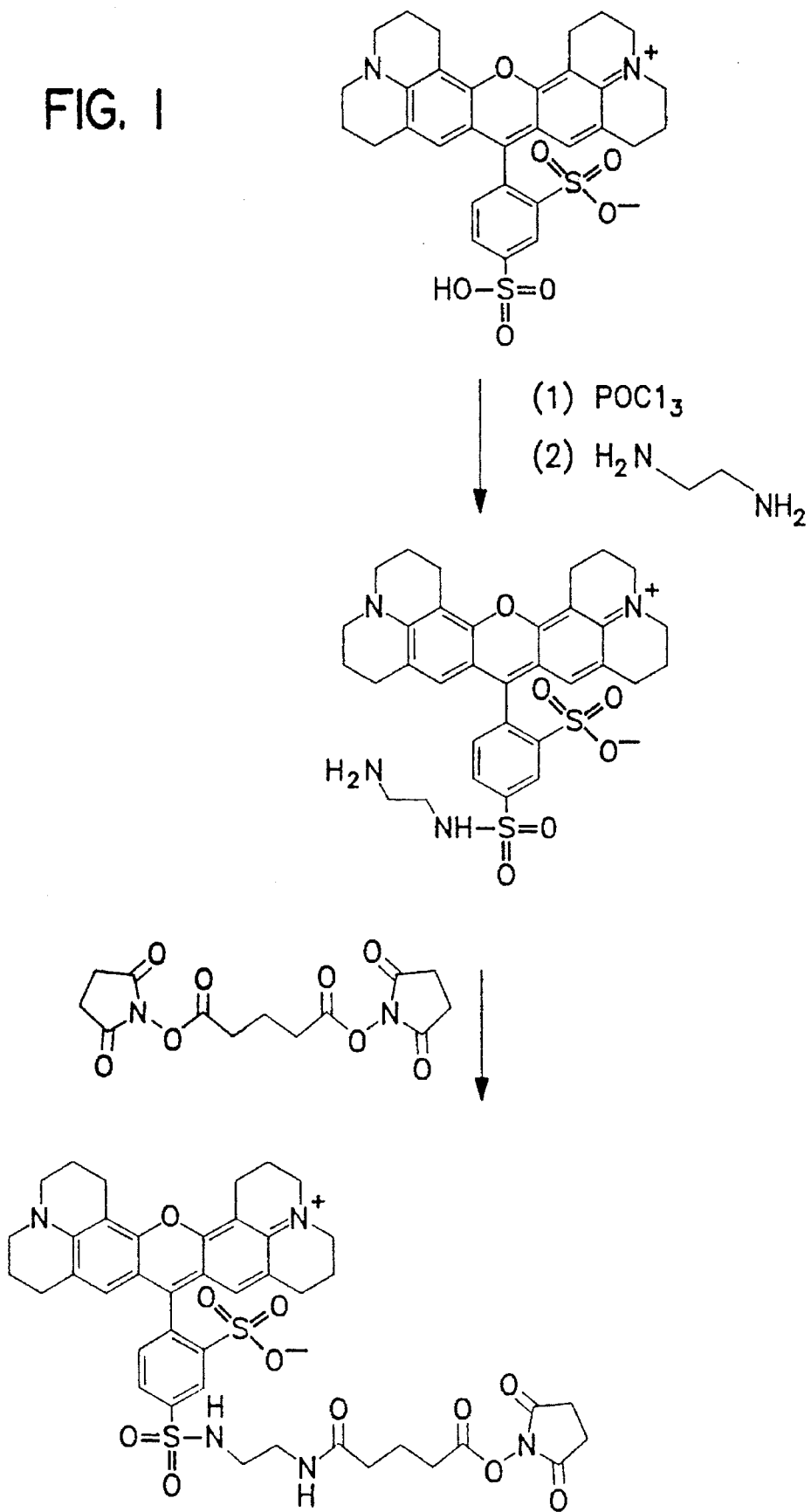
FIG. 1 illustrates the synthesis of an amine-reactive NHS ester fluorescent labeling reagent of General Formula I, wherein X is $CH_2CH_2$, Y is NHCO, Z is $CH_2CH_2CH_2$, and R is NHS ester.
Figure 2:
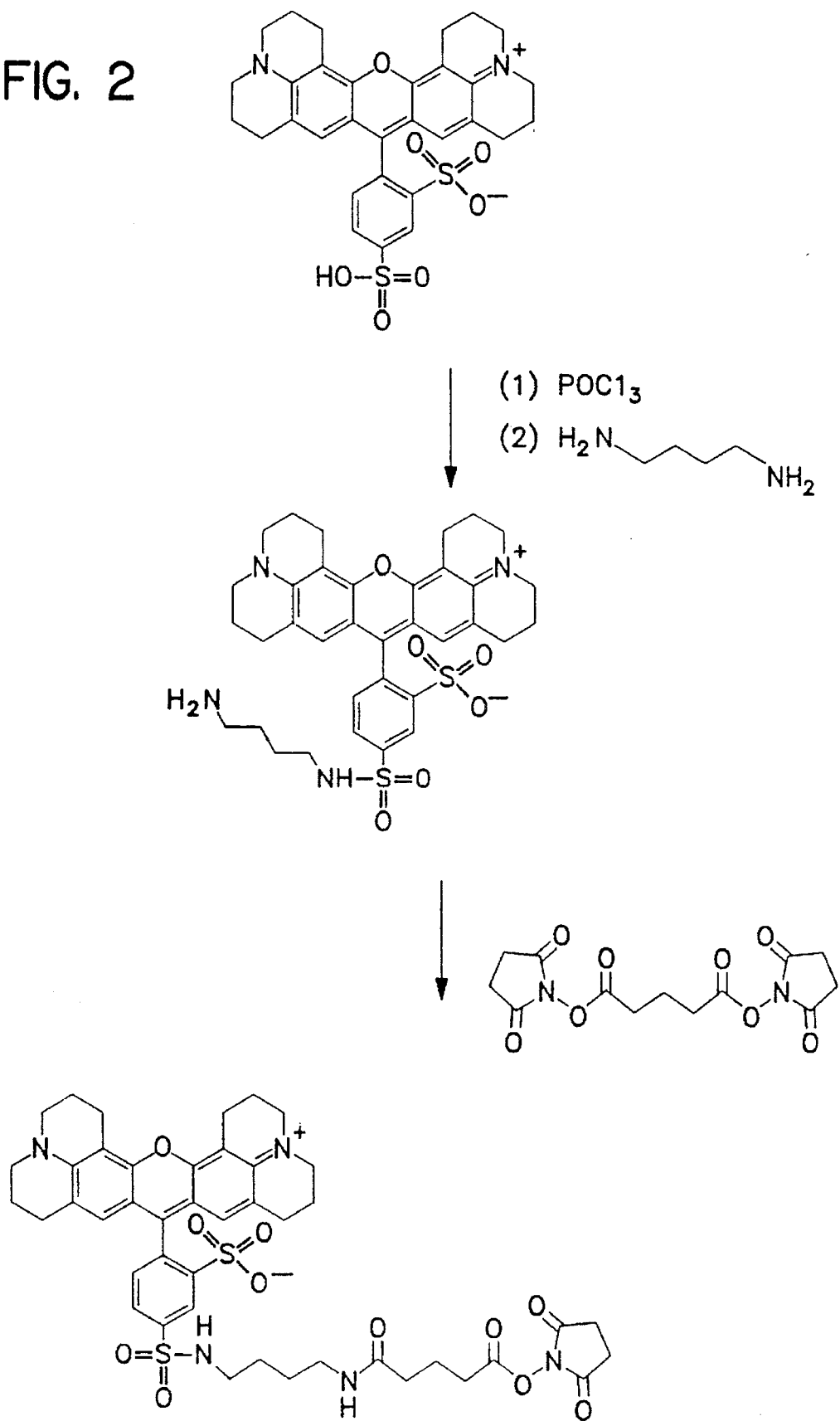
FIG. 2 illustrates the synthesis of an amine-reactive NHS ester fluorescent labeling reagent of General Formula I, wherein X is $CH_2CH_2CH_2CH_2$, Y is NHCO, Z is $CH_2CH_2CH_2$, and R is NHS ester.
Figure 3:
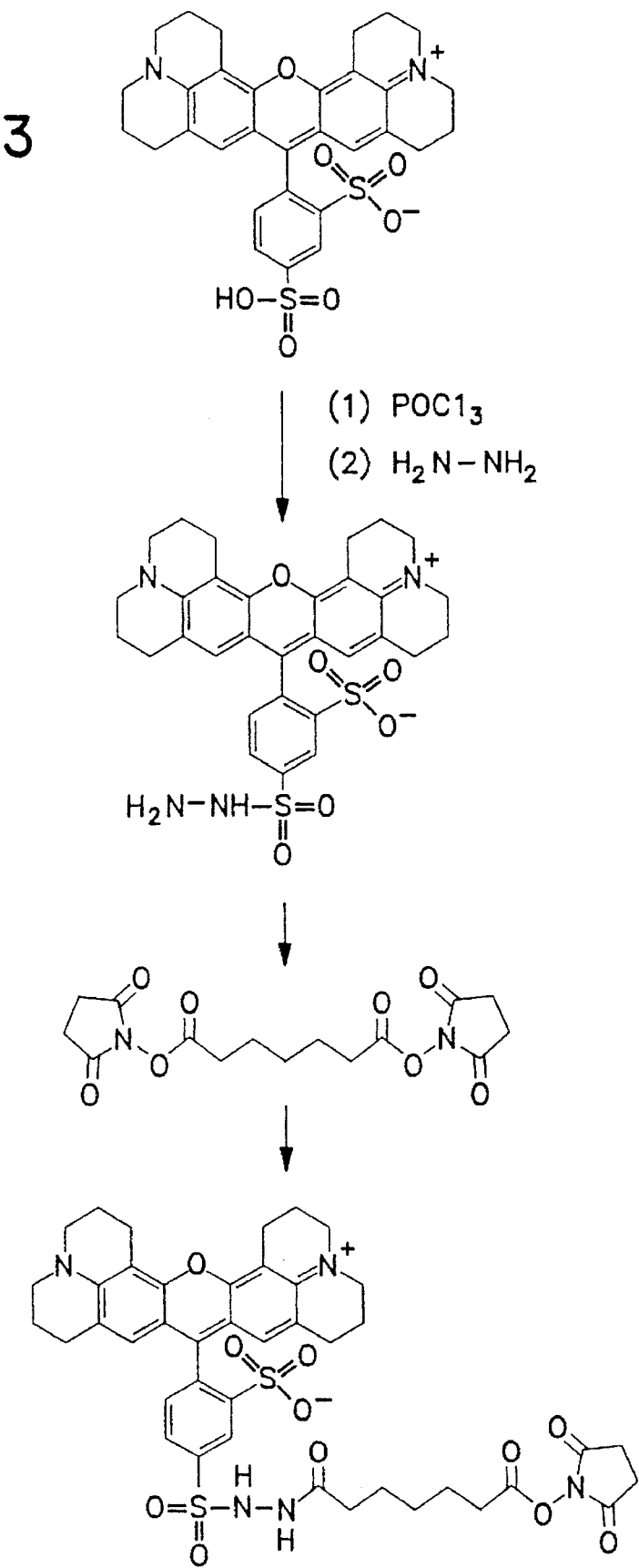
FIG. 3 illustrates the synthesis of a amine-reactive NHS ester fluorescent labeling reagent of General Formula I, wherein X is nothing, Y is NHCO, Z is $CH_2CH_2CH_2CH_2CH_2$, and R is NHS ester.
Figure 4:
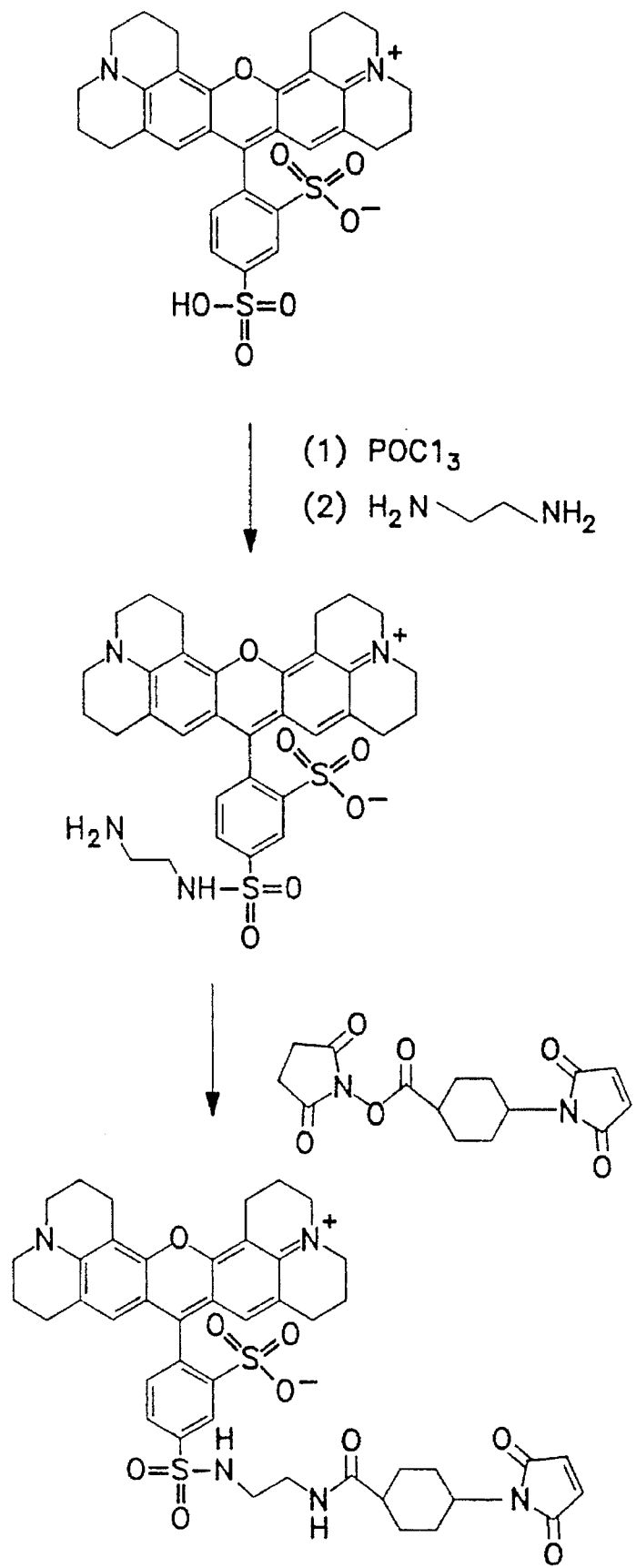
FIG. 4 illustrates the synthesis of thiol-reactive maleimide fluorescent labeling reagent of General Formula I, wherein X is $CH_2CH_2$, Y is NHCO, Z is cyclohexane, and R is a maleimide moiety.
Figure 5:
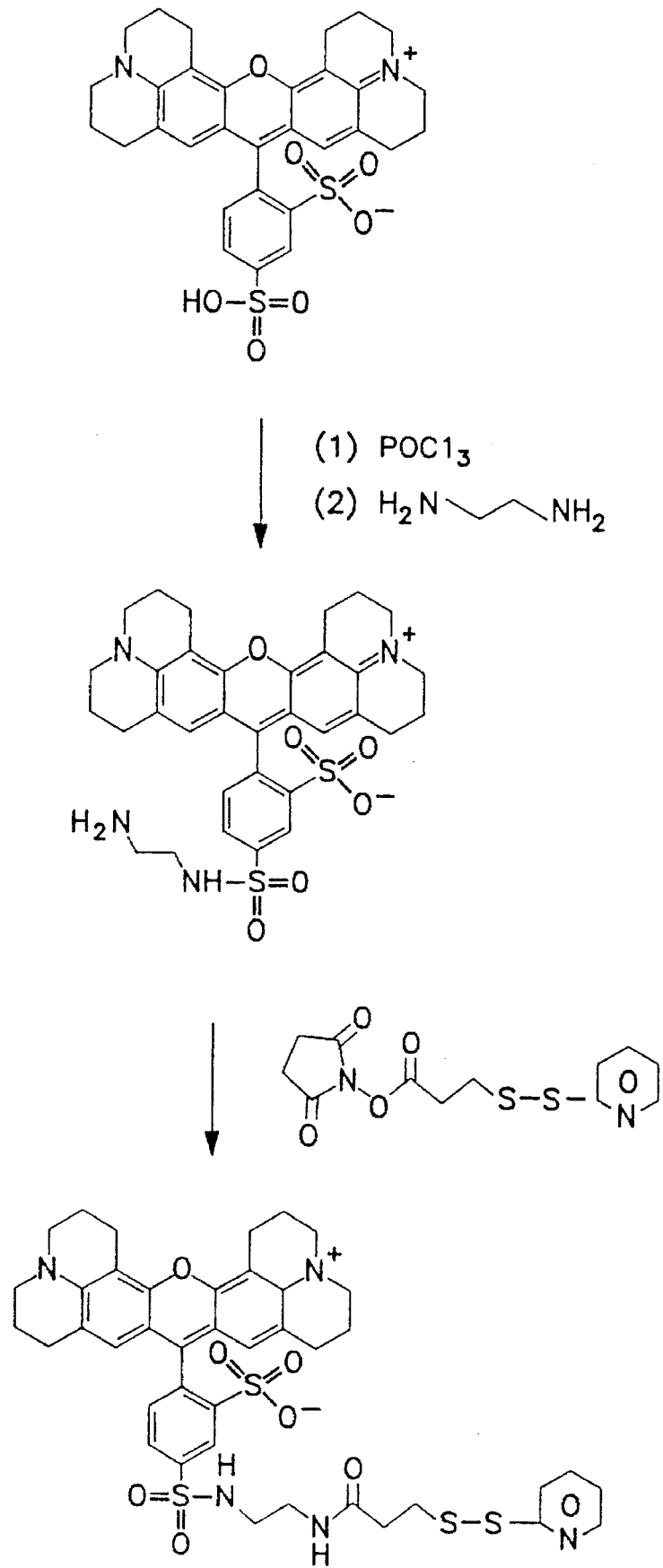
FIG. 5 illustrates the synthesis of a reactive disulfide fluorescent labeling reagent of General Formula I, wherein X is $CH_2CH_2$, Y is NHCO, Z is $CH_2CH_2$ and R is a pyridyl disulfide.
Figure 6:
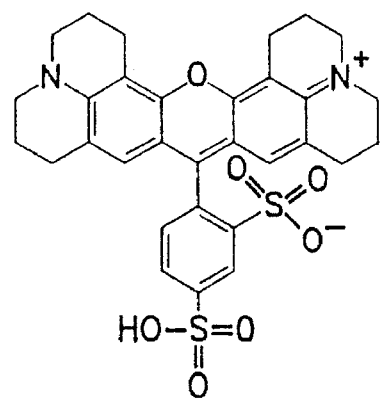
FIG. 6 illustrates the synthesis of a reactive amide fluorescent labeling reagent of General Formula I, wherein X is $CH_2CH_2$, Y is NHCO, Z is $CH_2CH_2CH_2$ and R is a substituted amide containing an imidazole moiety.
Figure 6:
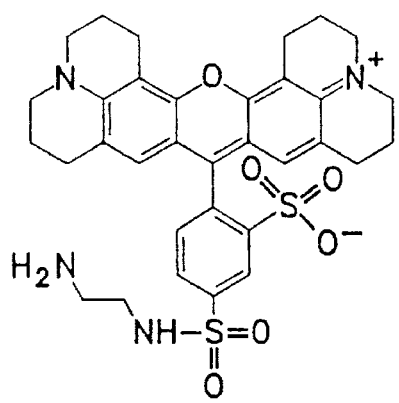
Figure 6:
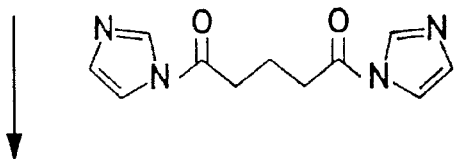
Figure 6:
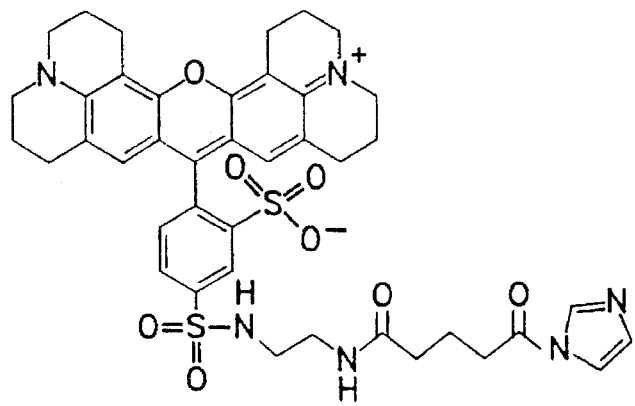
Figure 7:
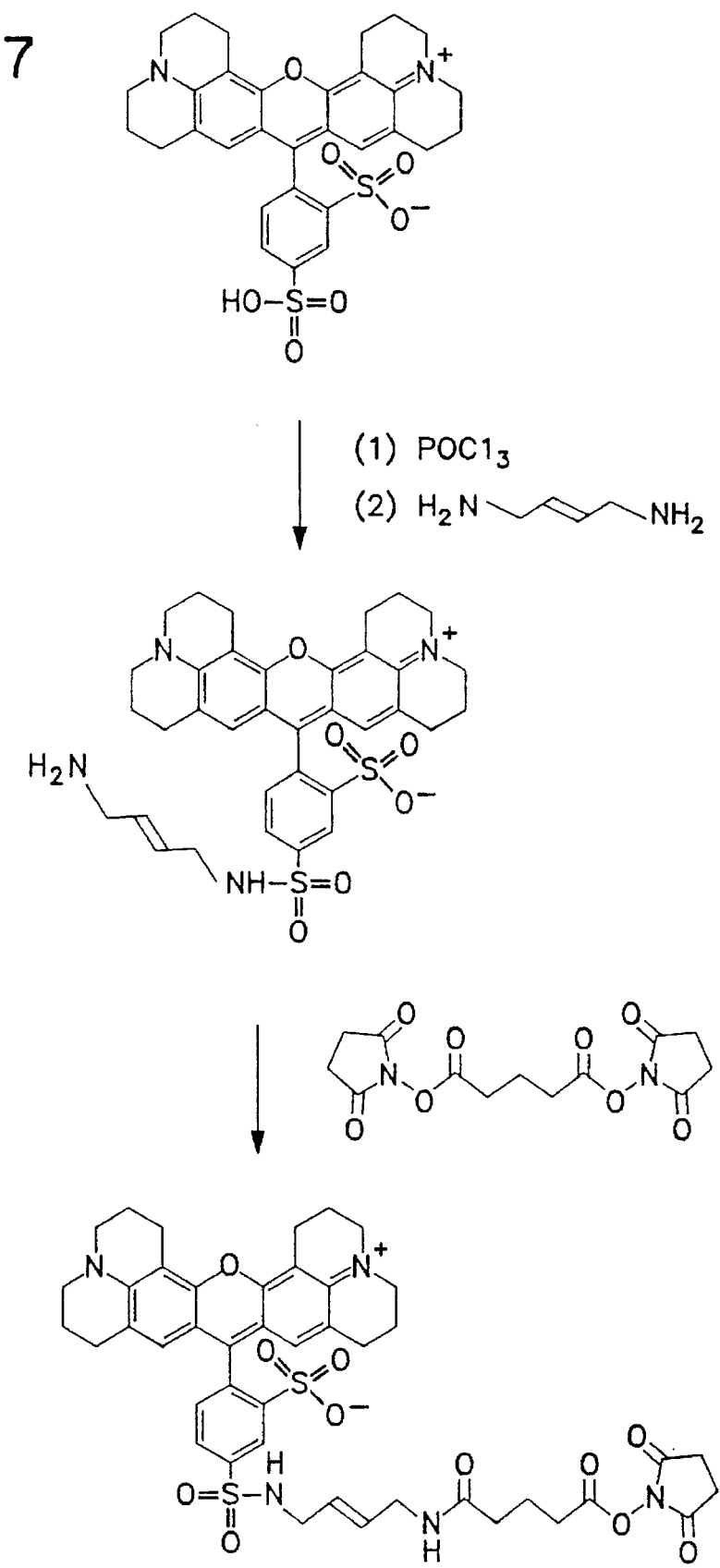
FIG. 7 illustrates the synthesis of an amine-reactive NHS ester fluorescent labeling reagent of General Formula I, wherein X is $CH_2CH=CHCH_2$, Y is NHCO, Z is $CH_2CH_2CH_2$, and R is NHS ester.

Labeling reagents suitable for the conjugation of a biomolecular species for the purpose of incorporating fluorescent properties have the general formula:

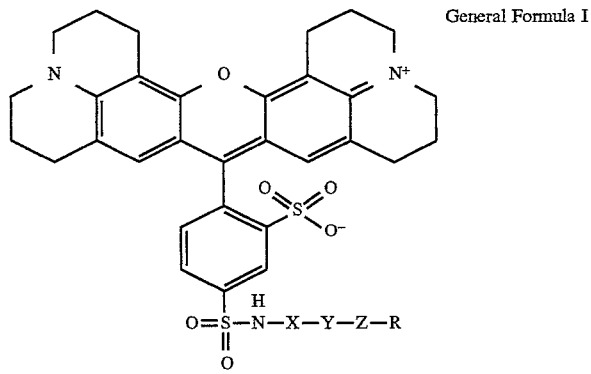

General Formula I

The group X is selected from an alkyl, an olefin, a monocyclic aliphatic saturated hydrocarbon, an aryl, or nothing at all. Alkyl denotes an acyclic saturated aliphatic straight or branched chain hydrocarbon. —$CH_2$, —$CH_2CH_2$, —$CH_2CH_2CH_2CH_2$— are examples of alkyls. A reasonably long alkyl chain may be used at group X because the overall reagent molecule is a zwiterion. —$CH_2CH=CHCH_2$— is an example of an olefin. An example of a monocyclic aliphatic saturated hydrocarbon is cyclohexane. An aryl is used to denote an aromatic ring, a substituted aromatic ring, and fused aromatic rings. Phenyl, hydroxyphenyl, and napthalene are examples of aryls.

The group Y is selected from an amide, a substituted amide, or nothing at all. An example of an amide is NHCO. An example of a substituted amide is $N(CH_3)CO$.

The group Z is selected from a monocyclic aliphatic hydrocarbon, an aryl, an alkyl or a polyethylene glycol chain of the general form $(CH_2CH_2O)_n$, or nothing at all. The alkyl or polyethylene glycol chain may further have inert intermediate functionalities, e.g., amide, ether, or disulfide functionalities. Again, a reasonably long alkyl chain may be used at group X because the overall reagent molecule is a zwiterion.

Groups X, Y, and Z can all be nothing or non-existent. However, groups X, Y, and Z cannot be nothing or non-existent at the same time. For example, an embodiment is contemplated where group X and group Y are nothing or do not exist, but group Z does exist, in the form of a monocyclic aliphatic hydrocarbon, an aryl, an alkyl or a polyethylene glycol chain of the general form $(CH_2CH_2O)_n$.

The group R is an electrophilic moiety suitable for conjugation of the fluorescent labeling reagent with a biomolecular species. Included as acceptable R groups are reactive esters, reactive amides, reactive disulfides, and substituted amide's containing maleimide functionalities. Suitable biomolecular species include proteins, peptides, hormones, oligonucleotides (RNA, DNA) and other nucleotides and their analogs, and liposomes.

Synthesis of the Sulforhodamine 101 Fluorescent Labeling Reagent

As illustrated in FIGS. 1 through 7, reagents of General Formula I, wherein X is selected from an alkyl, an olefin, a monocyclic aliphatic saturated hydrocarbon, an aryl, or nothing (e.g., X=0,1,2, . . . carbon equivalents in length), and Y is an amide are prepared by condensation of sulforhodamine 101 with a compound of the general formula $H_2N$—X—$NH_2$ followed by condensation with an NHS-ester derivative or reactive amide of the general formulas:

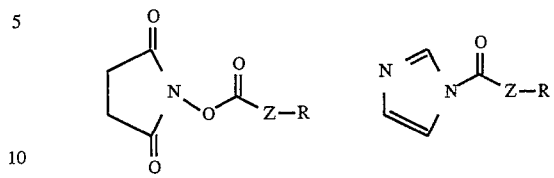

wherein Z is selected from a monocyclic aliphatic hydrocarbon, an aryl, an alkyl, as defined with respect to group X, a polyethylene glycol chain of the general form $(CH_2CH_2O)_n$, or nothing at all. The alkyl or polyethylene glycol chain may further have inert intermediate amide, disulfide, or ether functionalities. Group R is an electrophilic moiety suitable for conjugation of the fluorescent labeling reagent with a biomolecular species.

The synthesis of the labeling reagent of General Formula I is accomplished as follows. Sulforhodamine 101 is mixed with freshly distilled phosphorous oxychloride. The mixture is stirred slightly overnight. The phosphorous oxychloride is then removed at a vacuum pump to dryness. The sulforhodamine 101 is then dissolved in dry dimethyl formamide (DMF).

A diamine compound of the general formula $H_2N$—X—$NH_2$ is separately mixed with an amount of dry DMF. The sulforhodamine 101/DMF mixture is then added dropwise to the diamine mixture with vigorous stirring. The solution is then allowed to stir for 15 minutes. The solvents are then evaporated at the pump to dryness, and the residue is taken up in a few milliliters of methanol and partitioned between water and chloroform in a separatory funnel. The water layer is extracted three times with chloroform and the organic extracts are combined, dried, evaporated, and pumped dry to give the crude amine.

The crude amine is dissolved in chloroform and developed on two preparative TLC plates (1 mm thickness). After separation of the bottom amine band from the plate, the adsorbent is extracted four times with methanol and once overnight. The extracts are combined, reduced in volume, and poured into water. Upon extraction with chloroform, the dye solution is dried, filtered, evaporated, and pumped dry to yield a sulforhodamine 101 sulfonyl diamine of the general formula:

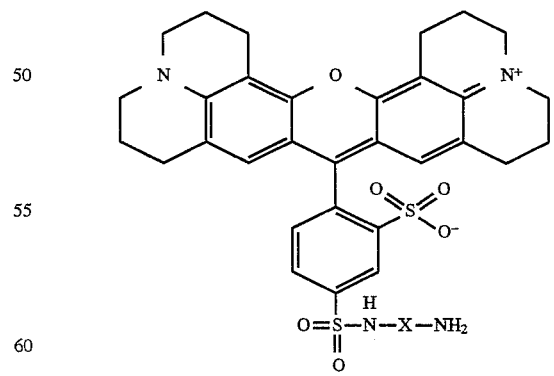

wherein X is selected from an alkyl, an olefin, a monocyclic aliphatic saturated hydrocarbon, an aryl, or nothing. Alkyl denotes an acyclic saturated aliphatic straight or branched chain hydrocarbon. —$CH_2$, —$CH_2CH_2$—, —$CH_2CH_2CH_2CH_2$— are examples of alkyls.

—$CH_2CH=CHCH_2$— is an example of an olefin. An example of a monocyclic aliphatic saturated hydrocarbon is cyclohexane. An aryl is used to denote an aromatic ring, a substituted aromatic ring, and fused aromatic rings. Phenyl, hydroxyphenyl, and napthalene are examples of aryls.

The sulforhodamine 101 sulfonyl diamine in DMF is inversely added under vigorous stirring to a NHS ester compound of the general formula:

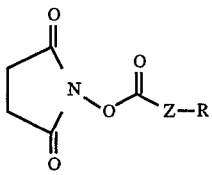

wherein Z is selected from a monocyclic aliphatic hydrocarbon, an aryl, an alkyl, as defined with respect to group X, a polyethylene glycol chain of the general form $(CH_2CH_2O)_n$, or nothing at all. The alkyl or polyethylene glycol chain of group Z may further have inert intermediate amide, disulfide, or ether functionalities. Group R is an electrophilic moiety suitable for conjugation of the fluorescent labeling reagent with a biomolecular species. Included as acceptable R groups are reactive esters, reactive amides, maleimides, and reactive disulfides. Example of reactive esters are NHS esters. Examples of reactive amides include imidazole functionalities. Examples of reactive disulfides include pyridyl disulfides.

The sulforhodamine 101 sulfonyl diamine/NHS ester solution is stirred for 15 minutes then evaporated in vacuo. The residue is taken up in chloroform and applied to four preparative TLC plates (1 mm thickness) with 15% MeOH/$CHCl_3$ as the eluant. The portion of the plate containing the product is removed and quickly exhaustively extracted with 15% MeOH/$CHCl_3$. The 15% MeOH/$CHCl_3$ solution is evaporated and the residue is dissolved in ethanol-free chloroform. The mixture is filtered, evaporated, and pumped dry to yield the product of General Formula I.

Alternatively, the product of General Formula I wherein group R is a reactive ester may be synthesized by dissolving the sulforhodamine 101 sulfonyl diamine of the general formula

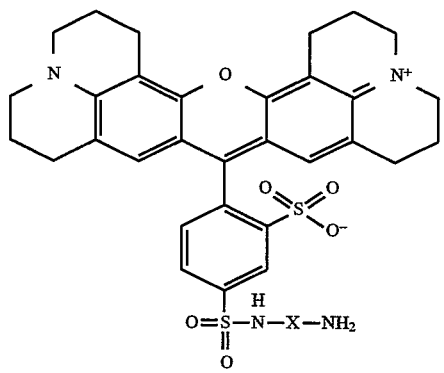

in dry pyridine followed by the addition of an acid anhydride of the general formula $Z(CO)_2O$, wherein Z is selected from a monocyclic aliphatic hydrocarbon, an aryl, or an alkyl, as defined with respect to group X, or a polyethylene glycol chain of the general form $(CH_2CH_2O)_n$. The alkyl or polyethylene glycol chain of group Z may further have inert intermediate amide, disulfide, or ether functionalities. The solution is allowed to stir for 15 minutes followed by the removal of the pyridine by evaporation. The residue is chromatographed on a silica gel column by dissolving it in a solution consisting of 10% MeOH/89.5% $CH_3Cl$/0.5% HOAc. The first fraction is eluted with this solvent mixture. When it has been cleared from the column, the acid fraction is chased through with 30% MeOH/69% $CH_3Cl$/1% HOAc and collected and the solvents are pumped dry to yield an acid of the general formula:

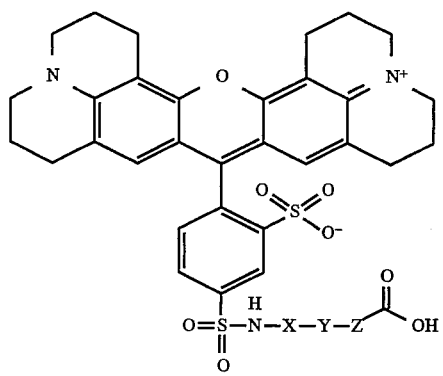

To this acid is combined an electrophilic compound R', wherein R' is selected from the group consisting of N-hydroxysuccinimido derivatives and N-hydroxymaleimido derivatives. The combination is stirred for a two day period. The mixture is then chromatographed on a preparative TLC plate followed by elution with 15% MeOH/$CH_3Cl$ to produce the compound of General Formula I.

Alternatively, the product of General Formula I wherein group Y is nothing and group R is a reactive ester may be prepared by dissolving a sulforhodamine 101-4-sulfonyl chloride in dry DMF and a pH 8.5 sodium carbonate solution containing a terminal amine substituted carboxylic acid of the general formula, $H_2NXCOOH$, in HCl, wherein X is selected from an alkyl, a monocyclic aliphatic saturated hydrocarbon, or an aryl. The mixture is stirred for one hour followed by evaporation of the volatile solvents. The residue is partitioned between $CH_3Cl/H_2O$ (pH 4) to remove the sulfonic acid. The organic layer is dried and evaporated. The product is dissolved in DMF and pyridine is added. To the solution is added a succinimdyl ester of the formula:

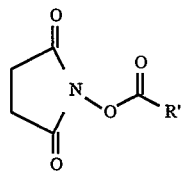

wherein R' is consists of an N-hydroxysuccinimido derivative. The combination is stirred for a two day period. The mixture is then chromatographed on a preparative TLC plate followed by elution with 15% MeOH/$CH_3Cl$ to produce the compound of General Formula I.

EXAMPLE I

Preparation of an Amine Reactive Sulforhodamine 101 Labeling Reagent of General Formula I The synthesis of an amine-reactive sulforhodamine 101 labeling reagent of General Formula I is outlined in FIG. 1.

In the initial step of the synthesis, sulforhodamine 101 (0.50 g, 6.5% water) was dried overnight at 100° C. under high vaccuum. The resulting dried powder is mixed with 3.0 mL of freshly distilled phosphorous oxychloride. The mixture is stirred slightly overnight. The phosphorous oxychloride is then removed at a vacuum pump to dryness. The sulforhodamine 101 is then dissolved in 10–20 mL of dry dimethyl formamide (DMF).

1,2-diaminoethane (5.14 mL) is separately mixed in a 100 mL flask with 25 mL of dry DMF. The sulforhodamine 101/DMF mixture is then added dropwise to the diamine mixture with vigorous stirring. The solution is then allowed to stir for 15 minutes. The solvents are then evaporated at the pump to dryness, and the residue is taken up in a few milliliters of methanol and partitioned between water and chloroform in a separatory funnel. The water layer is extracted three times with chloroform and the organic extracts are combined, dried ($Na_2SO_4$), evaporated, and pumped dry to give the crude amine.

The crude amine is dissolved in 5 mL of cloroform and developed on two preparative TLC plates (1 mm thickness). After separation of the bottom amine band from the plate, the adsorbent is extracted four times with methanol and once overnight. The extracts are combined, reduced in volume, and poured into water. Upon extraction with chloroform, the dye solution is dried, filtered, evaporated, and pumped dry to yield a sulforhodamine 101 sulfonylethylenediamine, 0.15–0.18 g (30–36%). Purer samples can be obtained by dissolving the amine in chloroform and precipitating with hexane.

Disuccinimdyl glutarate (0.6 g) in dry DMF (20 mL) under vigorous stirring is subjected to the inverse addition of a solution consisting of 140 mg of sulforhodamine 101 sulfonylethylenediamine (0.216 mmol) in 40 mL of dry DMF over 10 minutes. The sulforhodamine 101 sulfonylethylenediamine/NHS ester solution is stirred for 15 minutes then evaporated in vacuo. The residue is taken up in about 10 mL of dry chloroform and applied to four preparative TLC plates (1 mm thickness) with 15% MeOH/$CHCl_3$ as the eluant. The portion of the plate containing the product is removed and quickly exhaustively extracted with 15% MeOH/$CHCl_3$. If the analytical TLC test shows that the product solution is contaminated with disuccinimidyl glutarate, the combined product solutions are evaporated and again chromatographed on a single preparative TLC plate and worked up. Upon obtaining a satisfactory product, the 15% MeOH/$CHCl_3$ solution is evaporated and the residue is dissolved in ethanol-free chloroform. The mixture is filtered, evaporated, and pumped dry to yield the product of General Formula I approximately 110 mg (54%).

$^1$H NMR ($CDCl_3$) (500 MHz) (major isomer—4-sulfonamide) 8.75 (d, 1H, J=0.5 Hz, aromatic 3-H), 8.01 (dd, 1H, J=3, 1 Hz, aromatic 5-H), 7.61 (br s, 1H, amide H), 7.22 (d, 1H, aromatic 6-H), 6.84 (s, 2H, aromatic 1, 5-H), 3.34 (m, 8H, NC$\underline{H}_2$), 3.27 (m, 2, SNHC$\underline{H}_2$), 3.13 (m, 2, C$\underline{H}_2$NCO), 2.91 (m, 4H, ax. benzyl CH), 2.77 (s, 4H, NHS-H), 2.63 (m, 4H, eq. benzyl CH), 2.53 (t, 2H, C$\underline{H}_2$COONHS), 2.25 (t, 2H, NHCOC$\underline{H}_2$), 2.20–1.80 (m, 10H, —$CH_2$—); $R_f$=0.53 (silica, 15% MeOH/$CHCl_3$).

It is believed that the product of General Formula I, with the substituted 4-sulfonyl group, exists as an isomer, in at least a two to one ratio with the substituted 2-sulfonyl group.

Experiments have been performed that show that the compounds of the present invention can be reacted more controllably with a ligand (e.g., an antibody) than Texas Red. For example, these experiments demonstrate that the present invention reacts controllably with an antibody allowing consistent substitution ratios depending on the input ratios, while Texas Red produces more variable results, in some cases binding too many fluorophores to the antibody thereby tending to destroy the antibody's ability to bind to its target antigen. The present invention provides a more controllable substitution range over Texas Red.

In the preceding detailed description, the invention is described with reference to specific exemplary embodiments thereof. It will, however, be evident that various modifications and changes nay be made thereto without departing from the broader spirit and scope of the invention as set forth in the claims. The specification and drawings are, accordingly, to be regarded in an illustrative rather than a restrictive sense.

What is claimed is:

1. A method for preparing a molecular probe, comprising the steps of:

condensing sulforhodamine 101 with phosphorous oxychloride to form product P1:

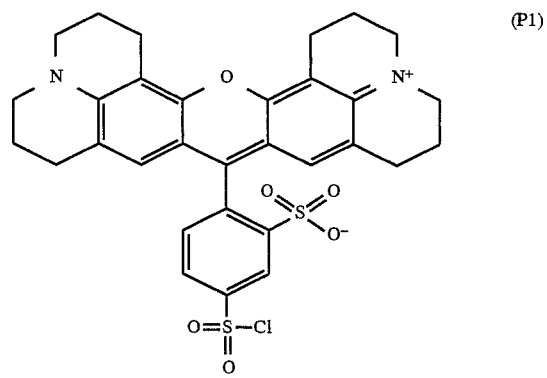

(P1)

condensing product P1 with $H_2NXNH_2$ wherein X is selected from an acyclic saturated aliphatic straight or branched chain hydrocarbon, an olefin, a monocyclic aliphatic saturated hydrocarbon, or an aryl, wherein aryl denotes an aromatic ring, a substituted aromatic ring, and fused aromatic rings, to form product P2:

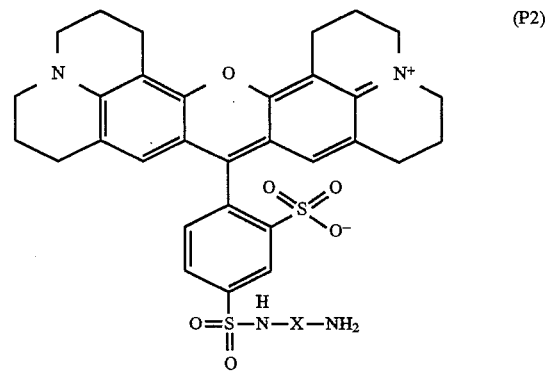

(P2)

condensing product P2 with a disuccinimidyl ester, a succinimidyl ester with a maleimide moiety, a succinimidyl ester with a diimidazolide, or a succinimidyl ester with a pyridyl disulfide to form products, P3a, 3b, 3c, 3d, respectively:

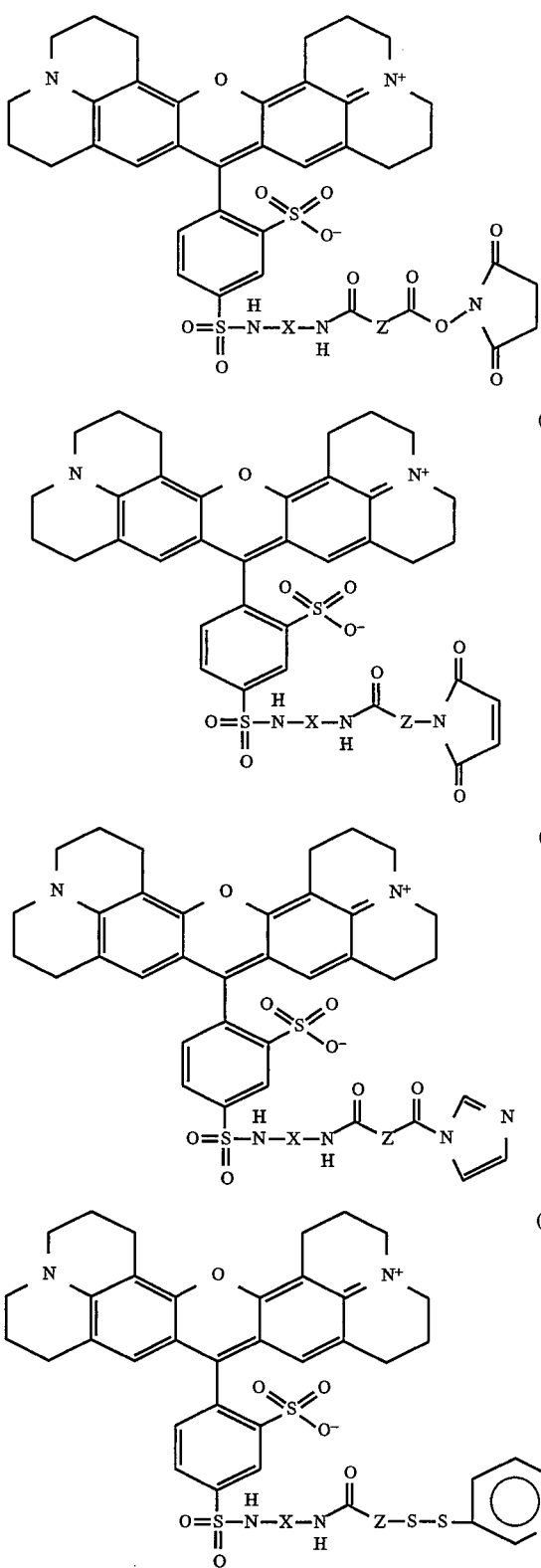

wherein Z is selected from a monocyclic aliphatic hydrocarbon, an aryl, and alkyl, or a polyethylene glycol chain of the general formula (CH₂CH₂O)n, wherein n=1–3, or nothing at all, wherein said alkyl or polyethylene glycol chain may further have inert intermediate amide, disulfide, or ether functionalities.

2. A method for preparing a molecular probe, comprising the steps of:

condensing sulforhodamine 101 with phosphorous oxychloride to form product P1:

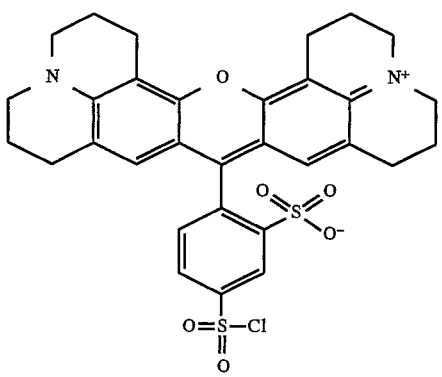

condensing product P1 with H₂NXNH₂, wherein X is selected from an acyclic saturated aliphatic straight or branched chain hydrocarbon, an olefin, a monocyclic aliphatic saturated hydrocarbon, or an aryl, wherein aryl denotes an aromatic ring, a substituted aromatic ring, and fused aromatic rings, to form product P2:

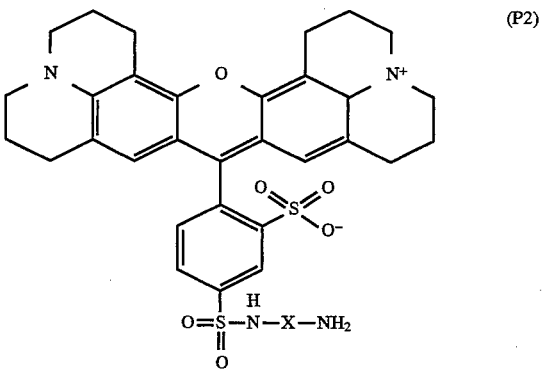

condensing product P2 with an acid anhydride of the general formula Z(CO)₂O, wherein Z is selected from a monocyclic aliphatic hydrocarbon, an aryl, or an alkyl or polyethylene glycol chain of the general formula (CH₂CH₂O)n, wherein n=1–3, to yield product P3:

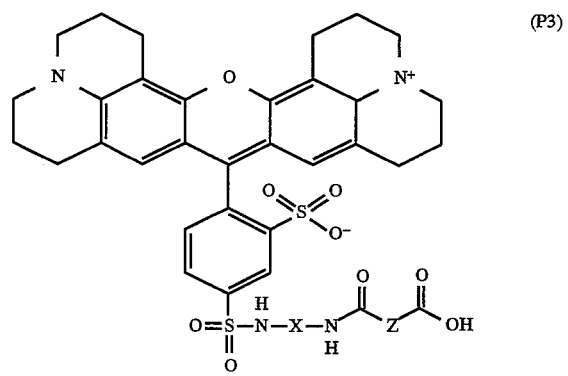

condensing product P3 with a disuccinimidyl carbonate or N-hydroxysuccinimide (NHS) and a carbodiimide.

* * * * *